(12) United States Patent
Becourt et al.

(10) Patent No.: US 7,732,431 B2
(45) Date of Patent: Jun. 8, 2010

(54) PHARMACEUTICAL COMPOSITIONS COMPRISING TRIMEGESTONE

(75) Inventors: Philippe Becourt, Massy (FR); Robert Georges, Bagnolet (FR); Serge Segot Chicq, l'Hay les Roses (FR)

(73) Assignee: aventis pharma SA, Antony (FR)

( * ) Notice: Subject to any disclaimer, the term of this patent is extended or adjusted under 35 U.S.C. 154(b) by 561 days.

(21) Appl. No.: 11/532,662

(22) Filed: Sep. 18, 2006

(65) Prior Publication Data

US 2007/0219169 A1 Sep. 20, 2007

Related U.S. Application Data

(63) Continuation of application No. 10/148,091, filed as application No. PCT/FR00/03240 on Nov. 22, 2000, now abandoned.

(30) Foreign Application Priority Data

Nov. 23, 1999 (FR) .................................. 99 14714

(51) Int. Cl.
*A61K 31/56* (2006.01)
(52) U.S. Cl. ...................... 514/170; 514/169; 514/177; 514/182
(58) Field of Classification Search ................ 514/170, 514/169, 177, 182
See application file for complete search history.

(56) References Cited

U.S. PATENT DOCUMENTS

| | | | | |
|---|---|---|---|---|
| 4,087,581 | A | * | 5/1978 | Vincent et al. ............... 428/327 |
| 4,761,406 | A | * | 8/1988 | Flora et al. ..................... 514/86 |
| 5,382,434 | A | * | 1/1995 | de Haan et al. .............. 424/465 |
| 5,384,419 | A | | 1/1995 | Buendia et al. |
| 5,399,685 | A | | 3/1995 | Buendia et al. |
| 5,547,948 | A | * | 8/1996 | Barcomb ..................... 514/170 |
| 5,759,577 | A | | 6/1998 | Barcomb et al. |
| 5,834,452 | A | | 11/1998 | Biton et al. |
| 5,858,405 | A | | 1/1999 | Gast et al. |
| 6,004,477 | A | * | 12/1999 | Nakagawa et al. ...... 252/188.28 |
| 6,063,403 | A | * | 5/2000 | de Haan et al. .............. 424/464 |
| 6,329,416 | B1 | | 12/2001 | Grubb et al. |

FOREIGN PATENT DOCUMENTS

WO   WO 98/04269   *   2/1998

OTHER PUBLICATIONS

McIlvaine buffer document (Whetten Ross, 1997).*

* cited by examiner

*Primary Examiner*—Sreeni Padmanabhan
*Assistant Examiner*—Umamaheswari Ramachandran
(74) *Attorney, Agent, or Firm*—Brian R. Morrill; Serena Farquharson-Torres

(57) ABSTRACT

The invention concerns a pharmaceutical composition comprises trimegestone optionally associated with an oestrogen, characterized in that it comprises a buffer solution whereof the pH, when it is introduced in the composition, ranging essentially between 2 and 5.5. The invention also concerns the methods for making such a composition and the primary package containing them.

19 Claims, No Drawings

PHARMACEUTICAL COMPOSITIONS COMPRISING TRIMEGESTONE

A subject of the present invention is pharmaceutical compositions comprising trimegestone, optionally combined with an estrogen, processes for their preparation and the primary packaging containing them.

Trimegestone is a steroid of the norpregnane series, (21S)-17alpha-methyl-17beta-(2-hydroxy-1-oxo-propyl)-oestra-4,9-dien-3-one known for its progestomimetic activity. It was described for the first time in the European Application EP-A-007823. Several publications report the very useful properties of this progestomimetic (replacement hormone treatment in the menopause, contraception). This compound can be used by itself or in combination with an estrogen: D. Ross et al. Maturitas (1977) 28(1) 83-88 27 (Suppl.) 64-A1-Azzawi et al. Hum Reprod. (1999) 14(3) 636-641-WO 9804269-A1-WO 9804268-A1; WO 9804265-A1; WO 9804246-A1.

The pharmaceutical compositions described in EP-A-0007823 are, in particular, those which can be administered orally, that is to say tablets, coated tablets, granules, cachets and capsules. These pharmaceutical compositions can be prepared by the conventional methods known to a person skilled in the art in the pharmaceutical formulation field, for example by moist granulation or by direct compression. Other pharmaceutical compositions comprising trimegestone are described in the European Applications EP-0722720-A1 or EP-0803250-A1.

Trimegestone in powder form is a molecule with a very low sensitivity to light and is stable after storage for 3 months at 70° C. under an inert gas or after storage for 6 months in a glass pill box at 50° C. Trimegestone is thus a molecule which is in itself stable. However, stability problems can appear during the preparation of tablets or if conventional pharmaceutical compositions comprising trimegestone are stored at 40° C. (dry or damp medium) or under more severe conditions. In particular, the appearance of (20S)-17alpha-methyl-7beta-(1-hydroxy-2-oxo-propyl)-oestra-4,9-dien-3-one, the 21R epimer of trimegestone, or even of oxopromegestone is observed under these conditions.

In order to avoid any stability problem, and in order to comply with standards in force in the field of pharmaceutical compositions, the Applicant has developed a new pharmaceutical composition essentially based on the addition of a buffer, the pH of which is between 2 and 5.5, and a novel moist granulation process. Other additives may advantageously be added to improve the stability and other properties required of a tablet.

A subject of the invention is thus a pharmaceutical composition in solid form intended for oral administration comprising trimegestone and optionally one or more estrogens, characterized in that it comprises a buffer, the pH of which is essentially between 2 and 5.5. The pH is measured at the time of incorporation of the buffer when carrying out the preparation process.

Among buffers which enable a pH of between 2 and 5.5 to be obtained there may be mentioned in particular the buffer formed by the combination of citric acid and disodium phosphate, the said compounds being in the hydrated form, where appropriate (monohydrate or dihydrate). Preferably, the pH of the buffer is essentially equal to 3.

A more particular subject of the invention is thus a pharmaceutical composition as defined above, characterized in that the buffer comprises a mixture of citric acid and disodium phosphate.

A quite particular subject of the invention is a pharmaceutical composition as defined above, characterized in that the mixture of citric acid and disodium phosphate has a pH essentially equal to 3.

The trimegestone can be combined with an estrogen. This estrogen can be 17beta-oestradiol (estradiol), estradiol valerate, ethynylestradiol, mestranol, quinestranol, estrone, a conjugated or esterified estrogen, estropipate or an estrogen of equine origin, such as Premarin®, it being possible for the said compounds to be in the hydrated form, where appropriate.

A more particular subject of the invention is thus the pharmaceutical composition as defined above comprising trimegestone and an estrogen.

A more particular subject of the invention is the pharmaceutical composition as defined above in which the estrogen is 17beta-oestradiol, in particular in the hemihydrate form.

A more particular subject of the invention is also the pharmaceutical composition as defined above, characterized in that the estrogen is Premarin.

Several additives may be provided in this pharmaceutical composition. It is thus possible advantageously to incorporate one or more binders, one or more lubricating agents, one or more opacifying agents, one or more chelating agents and one or more diluents.

Among the binders there may be mentioned cellulose derivatives, such as low-viscosity hydroxypropylmethylcellulose (HPMC), hydroxypropylcellulose (HPC), carboxymethylcellulose (CMC) or methylcellulose (MC), or also polyvidone, starch or gelatine. The binder will preferably be a cellulose derivative, in particular HPMC.

A more particular subject of the invention is thus the pharmaceutical composition as defined above, characterized in that it also comprises one or more binders, in particular a cellulose derivative.

A quite particular subject of the invention is thus the pharmaceutical composition as defined above, characterized in that the cellulose derivative is HPMC.

Among the lubricating agents there may be mentioned magnesium stearate, calcium stearate, zinc stearate, stearic acid, sodium stearyl fumarate, polyethylene glycol (PEG), talc and fatty acid esters, such as COMPRITOL® or MYVATEX®. The lubricating agent will preferably be stearic acid and/or talc.

A quite particular subject of the invention is thus the pharmaceutical composition as defined above, characterized in that it also comprises one or more lubricating agents, in particular stearic acid and/or talc.

A quite particular subject of the invention is also the pharmaceutical composition as defined above, characterized in that it also comprises one or more opacifying agents, in particular $TiO_2$.

Among the chelating agents there may be mentioned citric acid, ethylenediamine and phenylalanine.

A quite particular subject of the invention is thus the pharmaceutical composition as defined above, characterized in that it also comprises one or more chelating agents, in particular EDTA.

Among the diluents there may be mentioned maize starch, rice starch, potato starch, lactose, mannitol, cellulose and calcium derivatives, such as dicalcium phosphate. The diluent is preferably maize starch and/or lactose.

A quite particular subject of the invention is thus the pharmaceutical composition as defined above, characterized in that it also comprises one or more diluents, such as maize starch and/or lactose.

A quite particular subject of the invention is thus a pharmaceutical composition as defined above, characterized in that it comprises:
a) trimegestone, optionally combined with an estrogen, in particular estradiol,
b) a buffer comprising citric acid and disodium phosphate, the pH of which, when carrying out the preparation process, is essentially equal to 3,
c) if appropriate one or more binders,
d) if appropriate one or more lubricating agents,
e) if appropriate one or more opacifying agents,
f) if appropriate one or more chelating agents,
g) one or more diluents.

A quite particular subject of the invention is a pharmaceutical composition as defined above, characterized in that it comprises (% by weight)
- 0.05% to 3% of trimegestone
- 0.30% to 6% of estrogen
- 0% to 6% of a binder, such as HPMC
- 0% to 2% of an opacifying agent, such as titanium dioxide
- 0.1% to 2% of disodium phosphate/citric acid buffer, the pH of which when carrying out the preparation process is essentially equal to 3
- 0% to 4% of a lubricating agent, such as stearic acid and/or talc
- 0% to 0.2% of a chelating agent, such as EDTA
- qs diluent.

A quite particular subject of the invention is a pharmaceutical composition as defined above, characterized in that it comprises 0.2 to 0.8% trimegestone.

A quite particular subject of the invention is a pharmaceutical composition as defined above, characterized in that it comprises (% by weight)
- 0.4% trimegestone, 3.2% estradiol, 4% HPMC, 1% titanium dioxide, 0.15% anhydrous disodium phosphate, 0.4% citric acid monohydrate, 0.6% stearic acid, 1.2% talc, 0.1% EDTA, 31% maize starch, qs lactose.
- 0.8% trimegestone, 3.2% estradiol, 4% HPMC, 1% titanium dioxide, 0.15% anhydrous disodium phosphate, 0.4% citric acid monohydrate, 0.6% stearic acid, 1.2% talc and 0.1% EDTA, 31% maize starch, qs lactose.
- 0.25 mg trimegestone, 2.0 mg estradiol, 2.5 mg HPMC, 0.6 mg titanium dioxide, 0.1 mg anhydrous disodium phosphate,
- 0.25 mg citric acid monohydrate, 20 mg maize starch, 38.1 mg lactose, 0.4 mg stearic acid, 0.8 mg talc and 0.065 mg EDTA
- 0.5 mg trimegestone, 2.0 mg estradiol, 2.5 mg HPMC, 0.6 mg titanium dioxide, 0.1 mg anhydrous disodium phosphate, 0.25 mg citric acid monohydrate, 20 mg maize starch, 37.85 mg lactose, 0.4 mg stearic acid, 0.8 mg talc and 0.065 mg EDTA.

Another aspect of the invention is the process for the preparation of the tablets according to the invention. This is carried out using the moist granulation technique.

A more particular subject of the invention is the process for the preparation of the compounds according to the invention comprising the following stages:
1) Obtaining of granules of estrogen and trimegestone
   a) mixing of estrogen and trimegestone with a binder and one or more diluents, subsequently
   b) wetting by addition of an aqueous suspension comprising the buffer as defined above, a binder and an opacifying agent
   c) drying
   d) grading
2) Lubrication and
3) Compression.

According to a preferred embodiment relating to the composition comprising the two active ingredients, two types of granules comprising trimegestone and an estrogen respectively are first prepared, the two types of granules being mixed prior to the lubrication stage.

A subject of the invention is thus also the process for the preparation of the tablets according to the invention comprising the following stages:
1) Obtaining of estrogen granules
   a) mixing of estrogen with a binder and one or more diluents, subsequently
   b) wetting by addition of an aqueous suspension comprising the buffer as defined above, a binder and an opacifying agent
   c) drying
   d) grading
2) Obtaining of trimegestone granules
   a) mixing of a binder and one or more diluents, subsequently
   b) wetting by addition
      —of an aqueous suspension comprising the buffer, a binder and an opacifying agent
      —of trimegestone
   c) drying
   d) grading
3) Mixing of the granules of estrogen and trimegestone
4) Lubrication and
5) Compression.

The primary packaging can be the following:

The tablets to which the invention relates can be inserted into thermoformed packs (also called blisters). Another aspect of the invention thus relates to these thermoformed packs containing tablets of trimegestone optionally combined with an estrogen, according to the invention. These tablets are, in particular, 28 in number.

The thermoformed packs are preferably also inserted into a sachet under an inert atmosphere, and in particular under a nitrogen atmosphere.

These pharmaceutical compositions are of interest in the treatment of menopause symptoms and the prevention of post-menopausal osteoporosis. They can also be used as a contraceptive.

A subject of the invention is thus the use of trimegestone, optionally combined with an estrogen, for the preparation of a pharmaceutical composition according to the invention intended for treatment of menopause symptoms and prevention of osteoporosis.

Various methods of administration are described in Example 6, and a subject of the invention is the use of trimegestone, optionally combined with an estrogen, for the preparation of a pharmaceutical composition according to the invention intended for treatment of menopause symptoms, in which the said treatment is carried out by oral administration according to any one of the methods a) to e):

a)—of an estradiol tablet continuously in a dose of 0.5 to 2 mg per day for the first 14 to 18 days,
   —and of the tablet according to the invention comprising trimegestone (0.025 to 2 mg per day) and estradiol (0.5 to 2 mg per day) for the last 10 to 14 days of each cycle of 28 days (cycles of 28 days without interruption between the cycles),
b)—of an estradiol tablet in a dose of 0.5 to 2 mg per day for the first 14 to 18 days,
   —and of the tablet according to the invention comprising trimegestone (0.025 to 2 mg per day) and estradiol (0.5 to 2 mg per day) for the last 10 to 14 days, the treatment being stopped for 2 to 3 days per month at the end of each cycle of 28 days (cycle of 28 days per month), c)—of the tablet according to the invention comprising trimegestone (0.025 to 2 mg per day) and estradiol (0.5 to 2 mg per day) for the first 10 to 14 days, —and of an estradiol tablet in a dose of 0.5 to 2 mg per day for the last 14 to 18 days, the treatment being administered either without interruption between each cycle of 28 days or with an interruption of 2 to 3 days per month at the end of each cycle.

d)—of an estradiol tablet for the first 14 days in a dose of 0.5 to 2 mg per day, —and of the tablet according to the invention comprising trimegestone (0.025 to 2 mg per day) and estradiol (0.5 to 2 mg per day) during the last 11 days, the treatment being stopped for 5 to 6 days at the end of each cycle of 25 days, e)—of the tablet according to the invention comprising trimegestone (0.025 to 2 mg per day) and estradiol (0.5 to 2 mg per day) per day without interruption of the treatment.

A subject of the invention is also the use of trimegestone combined with an estrogen for the preparation of a pharmaceutical composition according to the invention, as a contraceptive. In this case a method of administration of the estroprogestogen composition for 21 to 25 days and interruption for 7 to 3 days will be used.

A subject of the invention is also a method for contraception by oral administration of the pharmaceutical compositions according to the invention.

The examples below illustrate the invention, but without limiting it.

EXAMPLE 1

Tablet of Trimegestone in a Dose of 0.25 mg 0.25 mg trimegestone, 2.0 mg estradiol, 2.5 mg HPMC, 0.6 mg titanium dioxide, 0.1 mg anhydrous disodium phosphate, 0.25 mg citric acid monohydrate, 20 mg maize starch, 3.81 mg lactose, 0.4 mg stearic acid, 0.8 mg talc and 0.065 mg EDTA.

EXAMPLE 2

Tablet of Trimegestone in a Dose of 0.5 mg 0.5 mg trimegestone, 2.0 mg estradiol, 2.5 mg HPMC, 0.6 mg titanium dioxide, 0.1 mg anhydrous disodium phosphate, 0.25 mg citric acid monohydrate, 20 mg maize starch, 37.85 mg lactose, 0.4 mg stearic acid, 0.8 mg talc and 0.065 mg EDTA.

EXAMPLE 3

Preparation of Tablets Comprising 0.500 mg Trimegestone and 2.0 mg Estradiol

A) Granules of Trimegestone (0.500 mg)

Stage 1: Preparation of the Buffer Solution 0.080 kg $Na_2HPO_4$ and 0.200 kg citric acid monohydrate are added to 10 liters of water and the mixture is stirred until solution is complete.

Stage 2: Preparation of Solution B 0.640 kg methylhydroxypropylcellulose 3 cp is added to the above solution (6.170 kg) and the mixture is stirred until solution is complete.

Stage 3: Preparation of Suspension C 0.800 kg micronized trimegestone and 0.480 kg micronized titanium dioxide are added to solution B and stirring is maintained until dispersion is complete.

Stage 4: Dry Mixing of Powders

The following constituents are mixed: methylhydroxypropylcellulose (HPMC) 3 cp (1.360 kg), maize starch (16.400 kg) and lactose monohydrate (51.040 kg).

Stage 5 Moist Granulation

The suspension of stage 3 (8.090 kg) is poured on to the powder mixture of stage 4 and 4.11 kg of the solution remaining from stage 1 are added.

Stage 6

The moist granules are then dried at 50° C. and subsequently graded.

B) Granules of Estradiol (2 mg)

The procedure is as for trimegestone, but the introduction of estradiol is carried out during stage 4. 3.2 kg estradiol are then used.

C) Preparation of Tablets Comprising the Two Active Ingredients (Lubrication Stage)

The moist granules of 0.500 mg trimegestone (51.04 kg) and 2 mg estradiol (51.04 kg) are mixed and a mixture comprising 0.640 kg micronized stearic acid and 1.28 kg talc is then introduced.

EXAMPLE 4

Comparative Stability Test

Tablet a (buffer pH 3): Trimegestone 1 mg, estradiol hemihydrate 2.0747 mg, hypromellose 3 cp 3.0 mg, titanium oxide 0.6 mg, disodium phosphate 0.0874 mg, citric acid monohydrate 0.2504 mg, maize starch 22 mg, lactose 44.4875 mg, magnesium stearate 0.5 mg and talc 1.0 mg: total weight 75.0 mg.

Tablet b (buffer pH 5): Trimegestone 1 mg, estradiol hemihydrate 2.0747 mg, hypromellose 3 cp 3.0 mg, titanium oxide 0.6 mg, disodium phosphate 0.219 mg, citric acid monohydrate 0.153 mg, maize starch 22 mg, lactose 44.4533 g, magnesium stearate 0.5 mg and talc 1.0 mg: total weight 75.0 mg.

These two tablets are kept for 15 days at 70° C. in a phial closed with a polyethylene stopper. The aim of this study is to determine the degradation products, in particular (20S)-(17beta-(1-hydroxy-2-oxo-propyl)-oestra-4,9-dien-3-one (product X), by HPLC. The detection threshold is 0.3%.

|  | Tablet a (buffer pH 3) | Tablet b (buffer pH 5) |
| --- | --- | --- |
| Product X | not detected | 0.85% |
| Total of impurities | 1.70 | 3.25 |

This study tends to demonstrate that the stability is not due solely to the presence of citric acid, but also to a pH effect.

EXAMPLE 5

Composition of the Blister and of the Sachet

The thermoformed packs comprise in particular of a transparent sheet of polyvinyl (chloride-acetate) (PVC) 200 μm thick, and an aluminium sheet comprising, from the outer surface to the inner surface:

a protective lacquer (nitrocellulose)
an aluminium sheet 20 μm thick,
a heat-sealable blue varnish (vinyl/acrylic)
a heat-sealable colourless varnish (vinyl/acrylic).

Furthermore, the sachet is, in particular, a three-layered sachet comprising, from the outer surface to the inner surface:
a polyurethane film
an aluminium sheet 9 μMm thick,
a laminating agent (polyurethane)
a polyurethane film 40 μm thick.

EXAMPLE 6

Plan for the Administration of the Combination of Trimegestone/estradiol in the Context of Treatment of Post-menopausal Symptoms and Prevention of Osteoporosis Continuous oral administration of an estradiol tablet (cycles of 28 days without interruption between the cycles) in a dose of 0.5 to 2 mg per day and of the tablet according to the invention comprising trimegestone for the last 10 to 14 days of each cycle of 28 days in a dose of 0.05 to 2 mg per day.

Oral administration of an estradiol tablet for 28 days per month in a dose of 0.5 to 2 mg per day and of the tablet according to the invention comprising trimegestone for the last 10 to 14 days of the administration of estradiol, in a dose of 0.05 to 2 mg per day. The treatment is stopped for 2 to 3 days per month at the end of each cycle of 28 days.

Oral administration of an estradiol tablet for 28 days per month in a dose of 0.5 to 2 mg per day and of the tablet according to the invention comprising trimegestone for the first 14 to 18 days of the administration of estradiol, in a dose of 0.05 to 2 mg per day. The treatment is administered either without interruption between each cycle of 28 days or with an interruption of 2 to 3 days per month at the end of each cycle.

Oral administration of estradiol for 25 days per month in a dose of 0.5 to 2 mg per day and of trimegestone in a dose of 0.05 to 2.5 mg per day for the last 11 days of the administration of estradiol. The treatment is stopped for 5 to 6 days at the end of each cycle of 25 days.

Continuous oral administration of estradiol in a dose of 0.5 to 2 mg per day and of trimegestone in a dose of 0.05 to 2.5 mg per day. There is no interruption of the treatment.

Continuous oral administration of estradiol in a dose of 0.5 to 2 mg per day and of trimegestone in a dose of 0.025 mg for 21 to 25 days and then a halt for 7 to 3 days.

In all these treatment methods, if the two active ingredients must be administered simultaneously, it is possible to use:
either a conventional estradiol tablet and a trimegestone tablet according to the invention,
or a mixed trimegestone/trimegestone tablet according to the invention.

The invention claimed is:

1. A pharmaceutical composition in solid form for oral administration, comprising by percentage of total weight:
   0.05% to 3% of trimegestone,
   0.30% to 6% of estrogen,
   0% to 2% titanium dioxide,
   0.1% to 2% of a buffer comprising citric acid and disodium phosphate, the pH of which is essentially between 2 and 5.5,
   0% to 4% of stearic, talc, or a combination of stearic acid and talc,
   0% to 0.2% of a chelating agent, and
   qs diluent.

2. The pharmaceutical composition of claim 1, wherein the estrogen is 17-beta-oestradiol.

3. The pharmaceutical composition as defined in claim 1, characterized in that the estrogen is of equine origin.

4. The pharmaceutical composition of claim 1, further comprising a binder.

5. The pharmaceutical composition of claim 4, wherein the binder is a cellulose derivative.

6. The pharmaceutical composition of claim 5, wherein the cellulose derivative is hydroxypropylmethylcellulose.

7. The pharmaceutical composition of claim 1, wherein the chelating agent is EDTA.

8. The pharmaceutical composition of claim 1 comprising by weight 0.2 to 0.8% of trimegestone.

9. A pharmaceutical composition in solid form for oral administration, which contains a buffer having a pH essentially between 2 and 5.5 and which composition comprises by percentage of total weight:
   0.4% of trimegestone,
   3.2% of estradiol,
   4% of HPMC,
   1% of titanium dioxide,
   0.15% of anhydrous disodium phosphate,
   0.4% of citric acid monohydrate,
   31% of maize starch,
   0.6% of stearic acid,
   1.2% of talc,
   0.1% of EDTA and
   qs of lactose.

10. A pharmaceutical composition in solid form for oral administration, which contains a buffer having a pH essentially between 2 and 5.5 and which composition comprises by percentage of total weight:
    0.8% of trimegestone,
    3.2% of estradiol,
    4% of HPMC,
    1% of titanium dioxide,
    0.15% of anhydrous disodium phosphate,
    0.4% of citric acid monohydrate,
    31% of maize starch,
    0.6% of stearic acid,
    1.2% of talc,
    0.1% of EDTA and
    qs of lactose.

11. A pharmaceutical composition in solid form for oral administration, which contains a buffer having a pH essentially between 2 and 5.5 and which composition comprises by percentage of total weight:
    0.25 mg of trimegestone,
    2.0 mg of estradiol,
    2.5 mg of HPMC,
    0.6 mg of titanium dioxide,
    0.1 mg of anhydrous disodium phosphate,
    0.25 mg of citric acid monohydrate,
    20 mg of maize starch,
    38.1 mg of lactose,
    0.4 mg of stearic acid,
    0.8 mg of talc,
    0.65 mg of EDTA, and qs diluent.

12. A pharmaceutical composition in solid form for oral administration, which contains a buffer having a pH essentially between 2 and 5.5 and which composition comprises by percentage of total weight:
    0.5 mg of trimegestone,
    2.0 mg of estradiol,
    2.5 mg of HPMC,
    0.6 mg of titanium dioxide, 0.1 mg of anhydrous disodium phosphate,
0.25 mg of citric acid monohydrate,
20 mg of maize starch,
37.85 mg of lactose,
0.4 mg of stearic acid,
0.8 mg of talc,
0.06 mg of EDTA, and qs diluent.

13. A process for the preparation of the pharmaceutical composition of claim 1, comprising the steps of:
   1) obtaining granules of the estrogen, the trimegestone, the buffer comprising citric acid and disodium phosphate, and a diluent;
   2) lubricating the granules; and
   3) compressing the granules.

14. The process of claim 13, wherein the step of obtaining the granules of the estrogen and trimegestone comprises the steps of:
   (a) preparing trimegestone granules that comprise trimegestone and the buffer comprising citric acid and disodium phosphate, and preparing estrogen granules that comprise the estrogen and the buffer comprising citric acid and disodium phosphate; and
   (b) mixing the trimegestone granules and the estrogen granules together.

15. The process of claim 14, wherein said pharmaceutical composition further comprises a binder and an opacifying agent, and the step of preparing the estrogen granules comprises the steps of:
   a) mixing estrogen with the binder and the diluent to form a mixture,
   b) adding an aqueous suspension of the buffer, a binder and the opacifying agent,
   c) drying the mixture, and
   d) grading the granules.

16. A thermoformed pack containing tablets comprising the pharmaceutical composition of claim 1.

17. The thermoformed pack of claim 16, wherein said pack is inserted into a sachet under an inert atmosphere.

18. A method of treating menopausal symptoms in female warm-blooded animals comprising orally administering to female warm-blooded animals in need thereof one of the following:
   a) an estradiol tablet continuously in a dose of 0.5 to 2 mg per day for the first 14 to 18 days, and a tablet comprising the pharmaceutical composition of claim 1 in which said estrogen is estradiol, such that trimegestone is administered in a dose of 0.25 to 2 mg per day, and estradiol is administered in a dose of 0.5 mg to mg per day, for at least 10 to 14 days of each cycle of 28 days without interruption between the cycles;
   b) an estradiol tablet in a dose of 0.5 to 2 mg per day for the first 14 to 18 days, and a tablet comprising the pharmaceutical composition of claim 1 in which the estrogen is estradiol, such that trimegestone is administered in a dose of 0.025 to 2 mg per day and estradiol is administered at a dose of 0.5 to 2 mg per day for the last 10 to 14 days, the treatment being stopped for 2/3 days per month at the end of each cycle of 28 days per month per dose,
   c) a tablet comprising the pharmaceutical composition of claim 1 in which the estrogen is estradiol, such that trimegestone is administered at a dose of 0.025 to 2 mg per day, and estradiol is administered at a dose of 0.5 to 2 mg per day for the first 10 to 14 days, and an estradiol tablet in a dose of 0.5 to 2 mg per day for the last 14 to 18 days, the treatment being administered either without interruption between each cycle of 28 days or with an interruption of 2 to 3 days per month at the end of each cycle,
   d) an estradiol tablet for the first 14 days in a dose of 0.5 to 2 mg per day and a tablet comprising the pharmaceutical composition of claim 1 in which the estrogen is estradiol, such that trimegestone is administered at a dose of 0.25 to 2 mg per day and estradiol is administered at a per dose of 0.5 to 2 mg per day for the last 11 to 14 days, the treatment being stopped for 5 to 6 days per month at the end of each cycle of 25 days, or
   e) a tablet comprising the pharmaceutical composition of claim 1 in which the estrogen is estradiol, such that trimegestone is administered at a dose of 0.025 to 2 mg per day and estradiol is administered at a dose of 0.5 to 2 mg per day, without interruption of the treatment.

19. A method of inducing contraception in female warm-blooded animals comprising orally administering to female warm-blooded animals in need thereof a contraceptively effective amount of the pharmaceutical composition of claim 1.

* * * * *

UNITED STATES PATENT AND TRADEMARK OFFICE
CERTIFICATE OF CORRECTION

| | | Page 1 of 1 |
|---|---|---|
| PATENT NO. | : 7,732,431 B2 | |
| APPLICATION NO. | : 11/532662 | |
| DATED | : June 8, 2010 | |
| INVENTOR(S) | : Philippe Becourt et al. | |

It is certified that error appears in the above-identified patent and that said Letters Patent is hereby corrected as shown below:

In column 1, line 3, below Title insert -- CROSS REFERENCE TO RELATED APPLICATIONS Continuation of Application No. 10/148,091, filed as application No. PCT/FR00/03240 on Nov. 22, 2000, now abandoned --.

In column 3, line 45, delete "EDTA" and insert -- EDTA, --, therefor.

In column 7, line 8, delete "9 μMm" and insert -- 9 μm --, therefor.

In column 9, line 7, in claim 12, delete "0.06mg" and insert -- 0.06 mg --, therefor.

In column 10, line 4, in claim 18, delete "mg" and insert -- 2 mg --, therefor.

Signed and Sealed this
Third Day of May, 2011

David J. Kappos
*Director of the United States Patent and Trademark Office*